United States Patent [19]

Sung

[11] 4,345,205

[45] Aug. 17, 1982

[54] FINISH MONITOR

[75] Inventor: Joseph P. Sung, Pensacola, Fla.

[73] Assignee: Monsanto Company, St. Louis, Mo.

[21] Appl. No.: 146,857

[22] Filed: May 5, 1980

[51] Int. Cl.³ .................................................. G01R 27/02
[52] U.S. Cl. .................................... 324/65 R; 118/665
[58] Field of Search ..................... 324/65 R, 65 P, 64, 324/54; 118/665

[56] References Cited

U.S. PATENT DOCUMENTS 2,608,604  8/1952  Hart ................................. 324/65 R
3,207,125  9/1965  Strandberg, Jr. ............ 324/65 R X
3,535,631  10/1970  DeGeest et al. ................... 324/65 R

FOREIGN PATENT DOCUMENTS 676126  7/1952  United Kingdom ............. 324/65 R
395704  1/1974  U.S.S.R. ........................... 324/65 R Primary Examiner—Stanley T. Krawczewicz
Attorney, Agent, or Firm—Kelly O. Corley

[57] ABSTRACT

In monitoring of yarn finish levels by conductivity, the yarn is grounded prior to the measurement, thus eliminating the effect of static electricity.

1 Claim, 1 Drawing Figure

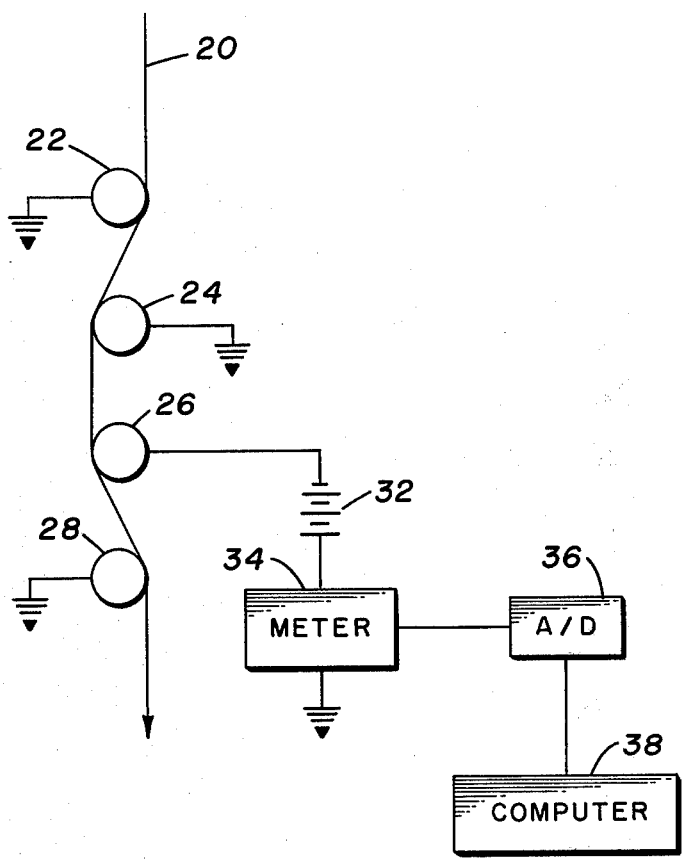

FINISH MONITOR

The invention relates to monitoring of yarn finish levels by conductivity.

Freshly formed man-made fibers or yarns are ordinarily coated with a liquid called a finish. The finish is typically a solution or emulsion of several ingredients, and is intended to perform various functions, such as lubrication, suppression of static, etc. For efficiency in many subsequent operations on the yarn, it is necessary that the finish level be accurately controlled. The present invention is directed to accurate measurement of the finish level on the running yarn.

According to the present invention, there is provided an apparatus for determining the level of finish on a running yarn, comprising, in combination, first and second conductive means for contacting the yarn at respective first and second points spaced along the path of the yarn; means for connecting the first conductive means to a point of fixed potential; and means for responding to the impedance along the portion of the yarn spanning the first and second conductive means.

According to another aspect of the invention, the last-named means comprises a closed series circuit comprising the first and second conductive means, the portion, a power source, and means for responding to current flow along the yarn between the first and the second conductive means.

According to another aspect of the invention, the apparatus further comprises a third conductive means for contacting the yarn at a point downstream of the second conductive means, and means for connecting the third conductive means to the point of fixed potential.

According to another aspect of the invention, the point of fixed potential is grounded.

Other aspects will in part appear hereinafter and will in part be obvious from the following detailed description taken together with the accompanying drawing, wherein:

The FIGURE is a schematic view of the preferred form of the invention.

As shown in the FIGURE, running yarn 20 passes among and contacts a series of conductive means at points spaced along the path of the yarn. The preferred form of conductive means is a conductive ceramic pin. Yarn 20 thus sequentially contacts guide pin 22, first pin 24, second pin 26 and third pint 28.

According to the invention, pin 24 is connected to a point of fixed potential, such as ground, preventing stray static charges accumulated upstream of pin 24 from interfering with the measurement. The finish level on the yarn is empirically related to impedance along the portion of yarn 20 spanning first pin 24 and second pin 26.

The impedance may be measured as follows. D.C. source 32 and meter 34 are serially connected between pin 26 and ground, so as to measure the current flow through the portion of yarn 20 spanning pins 24 and 26. The measured current flow is inversely related to the resistance of the spanning portion and, for a given finish composition, directly related to the finish level.

A signal proportional to the output of meter 34 (or the current therethrough) can be fed to an analog-to-digital converter 36, the output of which can be analyzed by computer 38 to determine finish level, coefficient of variance, etc.

Grounded electrode 28 prevents electrical disturbances originating downstream of itself from disturbing the measurement. When grounded electrode 28 is provided, the impedance measured is the impedance presented by the yarn segment spanning pins 24 and 26 in parallel with the yarn segment spanning pins 26 and 28.

As an example, D.C. source has an output of 45 volts, and pins 22, 24, 26 and 28 are about 12 mm. apart, and meter is a Keithley Model 480 picoammeter. With an apparel denier yarn and a particular finish, currents of the order of magnitude of a microampere are observed, which is well within the detection capability of the picoammeter.

What is claimed is:

1. Apparatus for determining the level of finish on a running yarn, comprising, in combination:
    a. first and second conductive means for contacting said yarn at respective first and second points spaced along the path of said yarn;
    b. means for connecting said first conductive means to a point of fixed potential;
    c. means for responding to the impedance along the portion of said yarn spanning said first and second conductive means, said last-named means comprising a closed series circuit comprising said first and second conductive means, said portion, a power source, and means for responding to current flow along said yarn between said first and said second conductive means; and
    d. a third conductive means for contacting said yarn at a point downstream of said second conductive means, and means for connecting said third conductive means to said point of fixed potential.

* * * * *